United States Patent [19]
Sneddon et al.

[11] Patent Number: 5,202,399
[45] Date of Patent: Apr. 13, 1993

[54] POLY(B-ALKENYL-BORAZINE) CERAMIC PRECURSORS

[75] Inventors: Larry G. Sneddon, Havertown, Pa.; Anne T. Lynch, Fairfield, Conn.

[73] Assignee: Truste of the University of Pennsylvania, Philadelphia, Pa.

[21] Appl. No.: 824,705

[22] Filed: Jan. 21, 1992

Related U.S. Application Data

[63] Continuation of Ser. No. 585,049, Sep. 18, 1990, abandoned, which is a continuation-in-part of Ser. No. 198,149, May 24, 1988, abandoned.

[51] Int. Cl.$^5$ .............................................. C08F 30/06
[52] U.S. Cl. ...................................................... 526/239
[58] Field of Search ......................................... 526/239

[56] References Cited

U.S. PATENT DOCUMENTS

| | | | |
|---|---|---|---|
| 2,917,543 | 12/1959 | Smalley et al. | 526/239 |
| 2,954,361 | 9/1960 | Graszos et al. | 526/239 |
| 2,954,366 | 9/1960 | Pellon | 526/239 |

OTHER PUBLICATIONS

Lynch, Anne T., Sneddon, Larry G., "Transition-Metal-Promoted Reactions of boron Hydrides, 12, Syntheses, Polymerizations, and Ceramic Conversion Reactions of B-Alkenylborazines", *Journal of the American Chemical Society*, 1989, 111, 6201.

*Boron Compounds 3rd Supplement*, vol. 3 (work through 1984).

Smalley et al., J. Am. Chem., Soc. 81, 1959, 582-586.

Gmelin Brochure, "This Is Gmelin".

Rice, R. W., *Ceram. Bull.*, 62, 889-892 (1983).

Wynne, K. J., Rice, R. W., *Ann. Rev. Mater. Sci.*, 14, 297-334 (1984).

Walker, B. E., Jr., Rice, R. W., Becher, P. F., Bender, B. A., Coblenz, W. S., *Ceram. Bull.*, 62, 916-923 (1983).

Bender, B. A., Rice, R. W., Spann, J. R., *Ceram. Eng. Sci. Proc.*, 6, 1171-1183 (1985).

Narula, C. K., Paine, R. T., Schaeffer, R., *Mat. Res. Soc. Symp. Proc.*, 73, 383-388 (1986).

Paciorek, K. J. L., Harris, D. H., Kratzer, R. H., *J. Polym. Sci., Polym. Chem. Ed.*, 1986, 24, 173-185.

Paciorek, K. J. L., Harris, D. H., Schmidt-Krone, W., Kratzer, R. H., Technical Report No. 4, 1987, Ultrasystems Defense and Space Inc., Irvine, CA.

Presentation of Rees, W. S., Jr., and Seyferth, D., at the 194th National Meeting of the American Chemical Society, Sep. 1987, Paper INOR 446 (J. Am. Chem. Soc., 71 [4], C-194-C-196 (1988)).

Pellon, J., Deichert, W. G., Thomas, W. M., *J. Polym. Sci.*, 55, 153-160 (1961).

Klancia, A. J., Faust, J. P., King, C. S., *Inorg. Chem.*, 1967, 6, 840-841.

Klancia, A. J., Faust, J. P., *Inorg. Chem.*, 1968, 7, 1037-1038.

Fritz, P., Niedenzu, K., Dawson, J. W., *Inorg. Chem.*, 1964 3, 626-627.

Sneddon, L. G., *Pure & Appl. Chem.*, vol. 59, No. 7, 837-846 (1987).

Narula, C. K., Schaeffer, R., Paine, R. T., Datye, A., Hammeter, W. F., *J. Am. Chem. Soc.*, 109, 5556-5557 (1987).

Narula, C. K., et al., "Precursors to Nonoxide Macromolecules and Ceramics", Polymer Preprints, (ACS, Div. Polym. Chem.) 1987, 28, 454.

Bracke, P., et al., "Inorganic Fibres and Composite Materials, A Survey of Recent Developments", Chapter 5, pp. 49-57 (Pergamon Press).

(List continued on next page.)

*Primary Examiner*—Joseph L. Schofer
*Assistant Examiner*—Alex H. Walker
*Attorney, Agent, or Firm*—Woodcock Washburn Kurtz Mackiewicz & Norris

[57] ABSTRACT

Novel poly(B-alkenyl-borazines), such as poly(B-vinyl borazine), are useful as precursors to BN ceramics. The poly alkenylborazines, which may advantageously be soluble and easily processed, are prepared by heat treatment of corresponding B-alkenylborazines, which are themselves novel compounds.

17 Claims, No Drawings

OTHER PUBLICATIONS

Wood, C., "Boron Carbides as High Temperature Thermoelectric Materials", AIP Conference Proceedings 140, pp. 362–372, (American Institute of Physics, 1986).

Kodama, G., et al., "Reactions of Pentaborane (9) with Ammonia, Characterization of the Diammoniate of Pentaborane (9)", *J. Amer. Chem. Soc.*, 94:2, 407 (1972).

Lynch, A. T., Sneddon, L. G., *J. Am. Chem. Soc., 1987, 109, 5867.*

Report No. AD/A158 658 reproduced by the National Technical Information Service, K. L. Paciorek et al., of Ultrasystems, Inc.

Mirabelli, M. G. L. and Sneddon L. G., *J. Am. Chem. Sci.*, 110, 449–453 (1988).

POLY(B-ALKENYL-BORAZINE) CERAMIC PRECURSORS

This is a continuation of application Ser. NO. 585,049, now abandoned, filed Sep. 18, 1990, which is a continuation of application Ser. No. 198,149, filed May 24, 1988, now abandoned.

BACKGROUND OF THE INVENTION

This invention relates to poly(B-alkenyl-borazine) ceramic precursors, to the novel B-alkenyl-borazines from which such ceramic precursors are made, to methods of synthesizing such ceramic precursors and B-alkenyl-borazines, and to methods of using such precursors to form boron nitride ceramics Pyrolysis of polymers to produce various carbon products, especially fibers, is widely practiced. One of the most important applications of this technology is in the preparation of carbon-carbon composites, where it is generally used to prepare both the fibers and the matrix. Carbon fibers made by pyrolysis were used in the first successful ceramic fiber composites and continue to be of interest in such applications. The lower costs, high strength and high Young's moduli of carbon fibers are strong attractions. However, these fibers are not very resistant to oxidation, and therefore their use in ceramic composites is limited. As a result, SiC-based fibers obtained by pyrolysis of polycarbosilanes have become the predominant material for use in ceramic fiber composite research and development studies Because of these and other high temperature environmental capabilities, an extensive interest in SiC-based fibers has occurred, even though strengths are typically lower and Young's moduli are substantially lower than those of most carbon fibers.

It has been pointed out that a variety of different precursors are needed if one is to produce a variety of ceramic compounds and/or mixtures for different applications. Rice, R.W., Am. Ceram. Soc. Bull., 1983, 62, 889-892. Such applications include bulk materials, matrices, fibers and coatings. Wynne, K.J., Rice, R.W., Ann. Rev. Mater Sci, 1984, 14, 297-334 have pointed out that the polymer pyrolysis technique offers several advantages over other preparative techniques, and that the technique is especially suitable to syntheses of silicon carbide and silicon nitride. The same article suggests that preceramic pyrolysis chemistry should find applications in the formation of boron nitride (BN) materials; however, until recently, little progress has been made in attempts to produce BN solid state materials in this fashion.

Polymers which yield boron nitride, BN, belong to one of the most important sets of precursors because BN and graphite have the same structure and bonding. Due to this similarity, BN has stiffness, strength and ablation characteristics that are comparable to those of graphite On the other hand, BN, an excellent dielectric material, has a very low dielectric constant and a low dielectric-loss factor in contrast to the high values of these two properties of graphite. BN also has a greater resistance to oxidation than graphite. Thus, BN provides the potential of making an oxidation-resistant body with strengths, stiffnesses, and ablation resistances comparable to those found in graphite.

BN polymer precursors are also of interest in the preparation of BN fibers, coatings, or as a matrix in ceramic-ceramic fiber composites. As a matrix for composites, it could be used with a variety of fibers. For instance, if one desired a composite with good dielectric properties, the use of fibers and matrix with good dielectric properties would be desirable. While fibers different from the matrix might be considered for this application, it is clear that BN fibers with a BN matrix would be preferred because of comparable dielectric behaviors.

There have been attempts to utilize polymer pyrolyses as low temperature alternatives to the preparation of BN. Inert atmosphere pyrolyses of various borazine derivatives, for example, led to reasonable yields of ceramic materials containing boron and nitrogen, but the materials also contained substantial amounts of carbon. Bender, B.A., Rice, R.W., Spann, J.R., Ceram. Eng. Sci. Proc., 6, 1171-1183 (1985). Narula, C.K., Paine, R.T., and Schaeffer, R. Mat. Res. Soc. Symp. Proc., 73, 383-388 (1986) report that oligomerization reactions of substituted borazines with silylamine cross-linking groups have been found to provide useful gel materials which upon pyrolysis form boron nitrogen materials. Other borazines indicated as possibly being suitable for pre-ceramics production include B-trianilinoborazine, B-triamino-N-triphenylborazine, and B-triamino-N-trimethylborazine. Pyrolysis of such compounds failed, however, to give pure boron nitride; carbon was invariably retained. Paciorek, K .J. L., Harris, D. H., Kratzer, R. H., J. Polym. Sci., Polym. Chem. Ed.. 1986, 24, 173-185. Polymers of tert. aminoborazine, anilinoborazine, phenylaminoborazine and aminoborazine were pyrolyzed in attempts to produce BN in Bender, B. A., Rice, R. W., Spann, J. R., Cer. Eng. Sci. Pro., 1961, 55, 153-160. Pyrolysis of the tert. aminoborazine gave no yield whatsoever, indicating complete decomposition to volatile species. The other three precursors gave measurable yields, with phenylaminoborazine and aminoborazine giving quite practical yields. The physical appearance of all the resultant pyrolysis products was dark gray to black, indicating a substantial carbon content.

The synthesis of BN from ammonia pyrolysis of soluble polyborazine compounds has been disclosed by Paciorek, K.J.L., Harris, D.H., Schmidt-Krone, W., and Kratzer, RH., Technical Report No. 4, 1987, Ultrasystems Defense and Space Inc., Irvine, California. In addition, it has recently been reported that ammonia pyrolysis of decaborane polymers linked by diamine molecules produced crystalline BN of high analytical purity. (Presentation of Rees, W.S., Jr. and Seyferth, D. at the 194th National Meeting of the American Chemical Society, September 1987, Paper INOR 446; J. Am. Ceram. Soc., 71 [4]C-194-C-196 (1988).)

There remains a clear need for a BN polymer precursor which will provide BN in high yields and high purity. Ceramic precursors which are processible are also greatly desired because they would allow the ceramic to be used in a variety of applications not presently commercially feasible. For example, if a soluble precursor to $B_4C$ were available, thin films of the solubilized precursor could be cast and pyrolyzed to yield thin films of the ceramic material. Similarly, a variety of substances could be coated with the soluble precursor material by various dipping or spraying techniques to yield, after thermal annealing, a substrate coated with the desired BN or $B_4C$ ceramic material. The soluble precursor might also be used to prepare spun fibers of ceramic material or in preparing a multitude of various ceramic/fiber composites.

The polymerization of certain olefinic boron-containing compounds was studied in Pellon, J., Deichert, W. G., Thomas, W.M., *J. Polym. Sci.*, 55, 153–160 (1961). In particular, the borazine (TAB) and B-trivinyl-N-triphenylborazine (TVB) was studied, and it was found that while TAB would homopolymerize, it was not very reactive, and TVB would not polymerize at all. It was postulated that the low or absent reactivity of these compounds was due to the steric effect of the flanking phenyl groups. The authors noted that they would have preferred to use a monovinylborazine with hydrogen on the adjacent nitrogens, but that synthetic difficulties had prevented that approach.

To date, Applicants are unaware of any publications relating to a method of synthesizing mono- or di-alkenylborazines. The synthesis of perfluorovinylborazines such as B,B'-dimethyl-B''-perfluorovinyl-N, N', N''-trimethylborazine and B,B',B''-tris(perfluorovinyl)-N,N',N''-trimethylborazine is disclosed in Klancia, A. J., Faust, J. P., King, C. S., *Inorg. Chem.*, 1967, 6, 840–841. Klancia, A. J. and Faust, J. P., in *Inorg. Chem.*, 1968, 7, 1037–1038, disclose a method for synthesizing B-vinylpentamethylborazine. The preparation of B-trivinylborazine by bubbling ammonia gas through bis(-dimethylamino)vinylborane is disclosed in Fritz, P., Niedenzu, K., and Dawson, J. W., *Inorg. Chem.*, 1964, 3, 626–627.

A method for preparing mono-vinyl borazines by reacting borazine with acetylene in the presence of a transition metal catalyst such as $Ir(CO)Cl[P(C_6H_5)_3]_2$ is disclosed in Sneddon, L. G., *Pure & Appl. Chem.*, 59, Vol. 7, pp. 837–846 (1987). A similar reaction using $RhH(CO)PPh_3)_3$ is disclosed in Lynch, A.T. and Sneddon, L.G., *J. Am. Chem. Soc.*, 1987, 109, 5867.

It is a object of this invention to provide ceramic precursor polymer materials rich in boron and nitrogen which can be pyrolyzed under mild conditions to yield BN ceramics in high purity and high yields. It is a further object of this invention to provide such ceramic precursors which are processible. These and other objects will be made clear from the following summary and discussion of this invention.

SUMMARY OF THE INVENTION

This invention relates to novel ceramic precursors which comprise condensation products of borazines mono- or di- B-substituted with an alkenyl group. The term "ceramic precursor" as used herein is intended to encompass monomers, oligomers or polymers which can be pyrolyzed to yield ceramic materials. The novel ceramic precursors can be substantially soluble, in which case they are easily processible, or they may be crosslinked.

This invention further relates to alkenyl-substituted borazines from which the aforementioned ceramic precursors are prepared. The alkenyl-substituted borazines of this invention have the general formula:

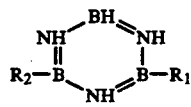

where one of $R_1$ and $R_2$ is an alkenyl group and the other of $R_1$ and $R_2$ is the same alkenyl group or is hydrogen. These borazine compounds may be N-substituted with various substitutents such as alkyl groups, aryl groups, halogen atoms, or haloalkyl groups, the selection of such substituents being limited only by the availability of starting materials. The preferred compounds, however, lack N-substituents.

This invention also relates to a process for preparing the novel mono- or di- B-alkenyl substituted borazines comprising contacting a B-unsubstituted borazine with an alkyne in the presence of a catalytic amount of a transition metal catalyst.

This invention also relates to a process for preparing the novel ceramic precursors of this invention, and to processes for converting those precursors to ceramic materials. Still further, this invention relates to articles such as ceramic films and ceramic coated substrates made using the novel ceramic precursors of this invention.

DETAILED DESCRIPTION OF THE INVENTION

A. Novel B-Alkenyl Borazines

Since a high BN/C ratio is generally desired in ceramics precursors, the preferred B-alkenyl borazine compounds of this invention are mono- B-substituted and are substituted with alkenyl groups having only two to three carbon atoms. The most preferred compound is B-vinyl borazine. However, borazines substituted with longer alkenyl groups, e.g., those having up to six carbon atoms, may also be prepared using the process of this invention.

The starting materials for the novel B-substituted borazines of this invention are the corresponding B-unsubstituted borazines. These B-unsubstituted borazines are contacted with the appropriate alkyne in the presence of a catalytic amount of a transition metal catalyst. Approximately stoichiometric quantities of the B-unsubstituted borazine and the alkyne are generally used, although a slight excess of either reactant may be preferred. It is generally preferred that the reaction be allowed to occur at relatively low temperatures, e.g., about room temperature, to prevent polymerization of the alkyne. This is especially so when the alkyne is acetylene which is readily polymerizable. Higher temperatures may be used with higher alkynes which do not polymerize as readily. For mono-substituted borazines the reaction is generally stopped after four to six hours. The product is then separated from the starting materials, which are recondensed over the catalyst, and the reaction is allowed to continue for an additional four to six hours. This is done to ensure that the production of di-substituted borazines is minimal. Different stoichiometry, longer reaction periods, and perhaps higher temperatures may be used to prepare di-substituted borazines.

The transition metal catalysts useful in preparing the B-alkenyl borazines are compounds well known in the art. The preferred catalysts are those in which the transition metal is one having eight d electrons, and the more preferred catalysts are those in which the transition metal is selected from Rh, Pd and Ir. Examples of transition metal catalysts are those which contain dissociable basic ligands, such as carbon monoxide or phosphines, e.g., $RhH(CO)(PPh_3)_3$, $Ir(CO)Cl[P(C_6H_5)_3]_2$, and $(Me_2C_2)Co_2(CO)_6$. Another class of transition metal catalysts which should be useful are those developed by P. M. Matilis, *Accts of Chem. Res.* 11, 301–307 (1978), the disclosure of which is hereby incorporated by reference. These catalysts do not contain basic ligands but are based on pentamethylcyclopentadienyl-rhodium and -iridium.

B. Poly(B-Alkenyl-borazines)

The liquid alkenylborazines may generally be converted to poly(B-alkenyl-borazines) by heating neat samples at a temperature of about 125° C. for about three to four hours under a vacuum. To prepare soluble poly(B-alkenyl-borazines), the alkenylborazines are heated in the presence of chain terminators under conditions effective to induce condensation but not to induce crosslinking, for example about 120° C. for up to about two hours. The preferred chain terminator is borazine, although others might also be effective. Best results have been obtained by the incorporation of about 50 mole % of borazine into the reaction mixture, the resulting polymer being substantially soluble and having only about 5% borazine actually incorporated therein. More stringent heat treatment (e.g., longer heating time and/or higher temperatures) are used to prepare the cross-linked poly(B-alkenyl-borazines). Preferably, cross-linked polymers are prepared by heating under a vacuum to a temperature of about 120° C. for three to four hours.

In addition to the aforementioned condensation methods, it should also be possible to condense the alkenylborazines by depositing them, e.g. by chemical vapor deposition, on a heated or chemically or photolytically activated surface. In such a method, the alkenyl borazines would polymerize on the surface of the substrate, creating a polymer coating on the substrate. The polymer coated substrate would then be further treated as described hereinafter to yield a ceramic coated substrate.

The term "substantially soluble" as used in this application is intended to encompass those poly(B-alkenyl-borazines) which are soluble (i.e., greater than 1.0 wt.%, but generally at least about 50 wt.%) in common organic solvents such as benzene, toluene and tetrahydrofuran. Further, for purposes of this invention, the term "substantially cross-linked" is intended to encompass those polymers which are not substantially soluble (i.e., less than 1 wt.%) in the above-mentioned common organic solvents. The advantages of a soluble ceramic precursor have already been discussed. By virtue of the processibility of the soluble precursor, the final ceramic material may be used in a variety of applications, such as thin films, fibers and coatings, not practically available using prior art precursors and methods. As another example of the use of the soluble precursor, one may dissolve hot pressed BN in the soluble precursor, draw a fiber from the resulting solution, and subject the fiber to pyrolyzing conditions to yield a BN fiber.

Using the above-mentioned methods, the alkenylborazines of this invention may also be condensed with other vinyl monomers, such as but not limited to styrene, ethylene, or propylene, to prepare novel copolymers. For example, polymers comprising about 99 to 10 weight % of the B-alkenyl borazine monomer and 1–90 weight % of one or more of the above-mentioned vinyl monomers could have a wide number of useful applications, such as being used for generating carbon-BN composite materials.

Although the emphasis in this application is on the use of the poly(B-alkenyl-borazines) as ceramic precursors, they may have uses other than those explicitly stated herein.

C. Pyrolysis to Boron Nitride

Pyrolysis of the above-described soluble or cross-linked poly(B-alkenyl-borazine) ceramic precursors can be achieved by methods known in the art. Generally, the precursors are slowly heated (5°–10° /min) under ammonia to a temperature in the range of about 500° to 1000° C.

Myriad uses exist for the ceramic materials which can be made as described above. They may be used, for example, to prepare refractory materials, fibers and composites. By virtue of the processibility of the non-crosslinked poly(B-alkenyl-borazine) precursors, the ceramic materials may be utilized in other applications not heretofore practical. For example, thin BN films may be made by casting thin films of the non-cross-linked polymer precursor and then pyrolyzing the film. In a similar manner, substrates such as but not limited to fibers and silicon chips may be coated with BN by coating the substrate with non-crosslinked polymer precursor and then subjecting the coated substrate to pyrolysis conditions. In both applications, the availability of a soluble ceramic precursor allows for preparation of the ceramic article under milder conditions than those required by the chemical vapor deposition methods which must be used with less processible precursors.

Although this description has focused on the preparation of BN ceramic materials via soluble polymer precursors, it is also possible to prepare such materials directly, without isolation of intermediates, from the alkenylborazine starting materials such as B-vinyl-borazine. Under suitable conditions, which could be easily determined by one skilled in the art, the alkenylborazines could be pyrolyzed to BN. For example, the alkenylborazine could be polymerized directly on a substrate surface by chemical vapor deposition and exposed to pyrolyzing conditions to effect pyrolysis of polymer to ceramic material.

Compounds of this invention and methods for preparing them are further illustrated in the following examples. These examples are intended to be illustrative only and are not intended to limit the scope of this invention.

EXAMPLE 1

Borazine (2.2175 g, 27.5 mmol) and acetylene (30 mmol) were reacted in the presence of $RhH(CO)(PPh_3)_3$ (0.0090g, $9.8\times10^{-3}$ mmol) for four hours at room temperature. Fractionation of the resulting reaction mixture gave 0.3056 g (2.87 mmol) of B-vinyl-borazine stopping in a $-70°$ C. trap and 1.890 g (23.5 mmol) of unreacted borazine. This corresponds to a 71.8% yield and 293 catalyst turnovers during the four hour period.

B-vinyl-borazine: $^{11}B$ NMR (160.5 MHz, ppm, $C_6D_6$): 31.5 (d, $B_{4,6}$, $J_{BH}=129$ Hz), 31.2 (s,$B_2$). $^1H$ NMR (200.13 MHz, ppm, $C_6D_6$): 4.5 (q, $J_{BH}=128$ Hz), 5.03 (t, $J_{NH}=49$ Hz), 5.72 (m, ABC pattern, J's calc. from PANIC simulation: $J_{HA-HB}=2.76$ Hz, $J_{HA-HC}=19.73$ Hz, $J_{HB-HC}=13.62$ Hz). Exact mass for $^{11}B_3{}^{12}C_2{}^{14}N_3{}^1H_8$, calcd. 107.0997; found 107.1000. IR spectrum (gas phase, NaCl windows, 10 cm cell): 3480 s, 3080 sh, m, 3070 m, 2980 m, 2970 m, 2600 m, 2520 vs, 2440 m, 1910 w, br, 1620 s, 1540 m, 1475 vs, br, 1425 s, sh, 1380 vs, 1350 s, sh, 1290 w, br, 1140 w, sh, 1125 m, 1120 m, 1015 m, 955 s, 930 vs, 920 vs, 735 s, 720 vs, 690 m, 680 m.

EXAMPLE 2

In a reaction analogous to that in Example 1, borazine (2.4723 g, 30.7 mmol) and propyne (30 mmol) were reacted in the presence of 0.0066g ($7.2 \times 10^{-3}$ mmol) of RhH(CO)(PPh$_3$)$_3$ for ten hours at 55° C. Fractionation of the resulting reaction mixture gave 0.364 g (3.02 mmol) of B-propenyl-B$_3$N$_3$H$_5$ stopping in a $-65°$ C. trap and 2.1868g (27.16 mmol) of unreacted borazine. This corresponds to a 85.2% yield and 419 catalyst turnovers during the ten hour period. GLC analysis of the product indicates that it is composed of a 80:20 mixture of B-trans−1-propenyl-B$_3$N$_3$H$_5$ and B-2-propenyl -B$_3$N$_3$H$_5$. Pure samples of each isomer were obtained by preparative GLC.

B-trans-1-propenyl-B$_3$N$_3$H$_5$: $^{11}$B NMR (160.5 MHz, ppm, C$_6$D$_6$) 31.6 (d, B$_{4,6}$, $J_{BH}=136$ Hz), 31.3 (S, B$_2$). $^1$H NMR (250.15 1.5 Hz) 4 52 (q BH, $J_{BH}=119$ Hz), 5.04 (t, NH, $J_{NH}=44.9$ Hz), 5.44 (d of d, CH, $J_{HB-HA}=17.7$, $J_{HB-CH3} =1.2$), 5.95 (d of q, CH, $J_{HA-HB}=18.0$ Hz, $J_{HA-CH3}=6.1$). Exact mass for 11 , calcd. 121.115; found, 121.113. IR spectrum (film, NaCl windows): 3440 vs, 3000 m, 2960 m, 2930 m, 2910 m, 2880 m, sh, 2850 m, 2600 sh, w, 2580 m, 2500 vs, 2440 m, sh, 2420 m, 1640 vs, 1460 vs, br, 1390 s, 1370 Vs, 1340 s, 1310 m, 1280 w, 1270 w, 1145 w, 1125 m, 1075 w, 1055 W, 1035 W, 980 s, 920 s, 900 Vs, 785 m, 715 s, 620 m.

B-2-propenyl-B$_3$N$_3$H$_5$: $^{11}$B NMR (160.5 MHz, ppm, C$_6$D$_6$): 31.6 (d, B$_{4,6}$, $J_{BH}=132$ Hz), 32.0 (S, B$_2$). $^1$H NMR (250.15 MHz, ppm, C$_6$D$_6$): 1.63 (s, CH$_3$), 4.76 (q, BH, $J_{BH}=127$ Hz), 5.19 (t, NH, $J_{NH}=50.0$ Hz), 5.27 (s, CH, br), 5.43 (s, CH, br). Exact mass for $^{11}$B$_3^{12}$C$_3^{14}$N$_3^1$H$_{10}$, calcd. 121.115; found 121.116. IR spectrum (film, NaCl windows): 3440 s, 3050 m, 2950 m, 2930 m, 2910 m, sh, 2850 w, 2580 w, sh, 2500 s, 2420 w, 1625 m, 1615 m, 1505 s, sh, 1460 vs, br, 1410 s, 1395 s, 1380 s, 1345 m, sh, 1330 m, 1260 w, 1080 w, 1040 w, 980 w, 920 s, 900 vs, 740 m, 715 s, 625 m.

EXAMPLE 3

As in the previous examples, borazine (1.618 g, 20.1 mmol) and 2-butyne (20 mmol) were reacted in the presence of RhH(CO)(PPh$_3$)$_3$ (0.0165 g, 0.018 mmol) for four hours at room temperature. Fractionation of the resulting reaction mixture gave 0.2702 g (2.01 mmol) of B-butenyl-borazine stopping in a $-55°$ C. trap. GLC analysis of the product indicates that it is composed of a 3:2 mixture of B-trans-(2-cis-butenyl)-borazine and B-trans-(1-butenyl)borazine. Pure samples of each isomer were prepared by preparative G.L.C.

B-trans-(2-cis-butenyl)borazine: $^{11}$B NMR (160.5 MHz, ppm, C$_6$D$_6$) 31.6(d, B$_{4,6}$, $J_{BH}=140.4$ Hz), 32.3(s,B$_2$). $^1$H NMR (250.15 MHz, ppm, C$_6$D$_6$): 1.48(s,CH$_3$), 1.55(d,CH$_3$, $J_{CH3-H}=6.95$ Hz), ~4.57 q, BH, $J_{BH}$116.6 Hz), 5.19(t, NH, $J_{NH}=51.5$ Hz), 5.81 q, CH, $J_{CH3-HB}=6.57$ Hz). Exact mass for $^{11}$B$_3^{12}$C$_4^{14}$N$_3^1$H$_{12}$, calculated 135.1296, found 135.1318. IR spectrum (film, NaCl windows): 3440 s, 3020 w, 2990 m, 2970 m, br, 2860 m, 2580 w, sh, 2510 s, 2440 w, br, 1630 s, 1460 vs, br, 1385 s, 1325 m, 1275 W, 1230 w, 1070 w, 1030 2, 980 w, 920 s, 905 Vs, 825 W, 715 s, 655 s.

B-trans-(1-butenyl)borazine: $^{11}$B NMR (64.2 MHz, ppm, C$_6$D$_6$): 33.8(d, $J_{BH}=126$ Hz), 34.0(s). $^1$H NMR(200 MHz, ppm, C$_6$D$_6$): 0.904(t, CH$_3$, $J_{CH3-CH2}=3$ Hz), 2.0(p, CH$_2$, J=7.1), ~4.43(q, BH, $J_{BH}=110$ Hz), 5.08(t, NH, $J_{NH}=44.7$ Hz), 5.43(d, CH$_A$, $J_{HA-HB}=16$. Hz), 6.06 (d of t, CH$_B$, $J_{HBHA}=17.6$, $J_{HBCH2}$ =6.1). Exact mass for $^{11}$B$_3^{12}$C$_4^{14}$N$_3^1$H$_{12}$, calculated 135.1296, found 135.1314.

EXAMPLE 4

Preparation of Crosslinked Poly(B-Vinyl-Borazine

A neat solution of vinyl-borazine was heated under vacuum at 130° C. for approximately four hours, resulting in the production of a hard, glassy, intractable crosslinked polymer. The polymer was insoluble in acetone, benzene, THF or DMF.

Elemental analysis Found C, 23.43; H, 6.98; N, 39.68; B, 29.54; Anal calculated for C$_2$B$_3$N$_3$H$_8$: C, 22.5; H, 7.5; N, 39.45; B, 30.41.

Thermogravimetric analysis of this polymer under Ar showed a slight weight loss between 200° and 300° C. (1.5%), a sharp weight loss from 500° to 700° C. (14%), followed by a slow tailing off from 700° to 1100° C. for an overall weight loss of 20.1%. Similar results were seen in the thermogravimetric analysis of this polymer under NH$_3$, the overall weight loss being 24%. Differential scanning calorimetry showed two small exotherms at 150° C. and 250° C., attributed to residual crosslinking, and a large exotherm at 550° C., which is consistent with TGA results.

Crosslinked polymers derived from propenyl-B$_3$N$_3$H$_5$ and butenyl-B$_3$N$_3$H$_5$ can be prepared in an analogous manner.

EXAMPLE 5

Preparation of Soluble Poly(B-Vinyl-borazine)

0.5516 g of vinyl borazine (5.18 mmol) and 0.2139 g of borazine (2.67 mmol) were condensed into a reaction flask. The mixture was stirred at 120° C. for approximately 3 hours. As the reaction progressed, the solution became increasingly viscous until the magnetic stirbar would no longer move. At this point the flask was frozen to $-196°$ C., and trace amounts of non-condensible gas were removed. The flask was then warmed to room temperature, and the volatile materials were removed in vacuo, leaving an air sensitive, viscous liquid identified as poly-2-(vinyl)borazine in approximately quantitative yield.

Poly-2-(vinyl)borazine: $^{11}$B NMR (160 MHz, ppm, C$_6$D$_6$): 30.5(d,2), 36.5(s,1). $^1$H NMR (500.135, ppm, C$_6$D$_6$): 0.90(m, br, 3), 4.9(br, 3). Ir spectrum (thin film, NaCl plates): 3440(vs), 2940(vs), 2900(vs), 2860(vs), 2730(w), 2580(s'sh), 2500(vs), 2420(s), 2280(w), 1905(w), 1810(w), 1600(m), 1420(vs,vbr), 1265(vs,br), 1220(vs,br), 1170(vs,br), 1085(s), 1065(s), 1000(vs), 920(vs), 865(s'sh), 845(s), 820(s), 750(vs'sh), 710(vs,br), 500(m,br).

The oligomer is soluble in common organic solvents such as benzene, toluene and THF, and had a broad weight range with fractions up to a molecular weight of about 1000 g/mol (GPC). (Molecular weights obtained by gel permeation chromatography were determined by comparison to polystyrene standards.) The $^{11}$B NMR of the oligomer is similar to that of the starting monomer, consisting of a low field singlet of intensity 1 attributed to the substituted B$_2$, and a higher field doublet of intensity 2. Upon polymerization, the single resonance at 31.2 ppm (monomer) was replaced by a new resonance at 36.5 ppm. This is consistent with the formation of a saturated polymer backbone since the shift of this resonance is similar to that of an alkyl-substituted borazine ring. (Noth, It., Wrackmeyer, B., *NMR 14: Basic Principles and Progress*, Diehl, P., Fluck, E., Kosfeld, R., Eds.;

Springler-Vearlag, NY (1978), 188–189) The IH NMR is also consistent with the formation of a linear oligomer, showing several broad aliphatic proton resonances in the 0.5 to 2 ppm region and no vinylic proton resonances ar 5–6 ppm. The infrared spectrum shows aliphatic C–H stretches from 2940–2730 cm$^{-1}$, a characteristic B–H stretch at 2500 cm$^{-1}$, and, most importantly, no evidence for a C=C absorbance.

Soluble polymers derived from B-propenyl-$B_3N_3H_5$ and B-butenyl-$B_3H_3H_5$ were prepared in an analogous manner.

EXAMPLE 6

Preparation of BN From Crosslinked Polymer

A sample of the precursor prepared in Example 4 was slowly heated under ammonia up to 1000° C., where it was held at this temperature for four hours. This resulted in the formation of a light brown, completely amorphous compound identified as BN in a ceramic yield of 72%. Elemental Analysis: Anal calcd for BN: B, 43.55; N, 56.45; Found: B, 38.82, N, 49.52; C, 3.71; H, 0.34. IR(Diffuse): 3450(s), 2800(m,br), 2550(m,br), 2350(m,br), 1450(vs,br), 1100(s), 850(m), 720(vs), 700(s,br), 625(m). Elemental analysis of the product shows a B/N ratio of 1.02 with measured levels of carbon of 3.71%. Diffuse reflectance IR is consistent with spectra previously reported for BN. (Brame, E.G., Jr., Margrave, J.L., Meloche, V.W., *I. Inorg. NuCl Chem.* 5,a 48–52 (1957); Takahashi, T., Itoh, H., Takeuchi, A., J. Crystal Growth. 47, 245–250 (1979).)

EXAMPLE 7

Preparation of BN from Soluble (Non-Crosslinked) Poly(vinylborazine)

Poly(vinylborazine) (734 mg) dissolved in diethylether was placed into a fused silica boat, in a tube furnace under a flow of ammonia (100 ml/min). The sample was slowly heated (5° C./min) to 550° C. and it was held at this temperature for one hour. The sample was then further heated at a rate of 10° C./min to 1000° C. and held at this temperature for an additional hour. After cooling to room temperature, a light brown material (540.5 mg, 73.6% yield) was obtained with the composition $B_{0.99}N$. Elemental analysis: cald for BN: B, 43.55; N, 56.45; found: B, 41.67; N, 54.84;° C., 1.30; H, 0.40. IR(diffuse): 3450(s), 2800(m,br), 2550(m,br), 2350(m,br), 1450(vs,br), 1100(s), 850(m), 720(vs), 700(s,br), 625(m).

What is claimed is:

1. Polymers comprising condensation products of borazines which are mono- or di-b-substituted with an alkenyl group and which are substituted at each N-atom with hydrogen.

2. The polymers of claim 1 which are condensation products of mono- B-alkenyl borazines.

3. The polymers of claim 1 where the alkenyl group has two to three carbon atoms.

4. The polymers of claim 2 where the alkenyl group has two to three carbon atoms.

5. The polymers of claim 1 which is the condensation product of B-vinyl-borazine.

6. The polymers of claim 1 which are substantially soluble.

7. The polymers of claim 2 which are substantially soluble.

8. The polymers of claim 3 which are substantially soluble.

9. The polymers of claim 4 which are substantially soluble.

10. The polymers of claim 5 which are substantially soluble.

11. A process for preparing substantially soluble polymers comprising heating a mono- or di-B-alkenyl borazine which is substituted at each N-atom with hydrogen and a chin terminator under conditions effective to induce condensation o the mono- or di- B-alkenyl borazine but not to induce cross-linking of said polymers.

12. The process of claim 16 in which said heating is carried out under a vacuum or in an inert gas atmosphere.

13. The process of claim 11 in which said mono- or di-B-alkenyl borazine is heated under a vacuum to a temperature of about 120° C. for a period of up to about two hours.

14. A process for preparing substantially crosslinked polymers comprising heating a mono- or di- B-alkenyl borazine under conditions effective to induce crosslinking of said product.

15. The process of claim 14 in which said heating is carried out under a vacuum or in an inert gas atmosphere.

16. The process of claim 14 in which said mono- or di-B-alkenyl borazine is heated under a vacuum to a temperature of about 120° C. for about three to four hours.

17. The composition of claim 1 wherein said substituted borazines comprises the reaction product of B-unsubstituted borazines with an alkyne in the presence of a catalytic amount of a transition metal catalyst.

* * * * *